United States Patent
Heim et al.

Patent Number: 5,897,534
Date of Patent: Apr. 27, 1999

[54] BODY FLUIDS AND SOLIDS DRAINAGE SYSTEM

[75] Inventors: Warren P. Heim; James Lawrence Brassell, both of Boulder, Colo.

[73] Assignee: Team Medical, LLC, Boulder, Colo., CO

[21] Appl. No.: 08/705,181

[22] Filed: Aug. 29, 1996

[51] Int. Cl.$^6$ .................................................. A61M 25/00
[52] U.S. Cl. .......................... 604/267; 604/19; 604/266
[58] Field of Search ................................. 604/266–268, 604/317, 319, 22, 27, 35, 36, 19; 137/205

[56] References Cited

U.S. PATENT DOCUMENTS

| | | | |
|---|---|---|---|
| 1,485,298 | 2/1924 | Schroyer . | |
| 3,320,957 | 5/1967 | Sokolik | 128/311 |
| 3,982,540 | 9/1976 | Ross | 128/278 |
| 4,228,802 | 10/1980 | Trott . | |
| 4,372,336 | 2/1983 | Cornell et al. | 137/205 |
| 4,439,190 | 3/1984 | Protzmann et al. | 604/319 |
| 4,465,483 | 8/1984 | Weilbacher | 604/317 |
| 4,728,319 | 3/1988 | Masch | 604/22 |
| 4,790,812 | 12/1988 | Hawkins, Jr. et al. | 604/22 |
| 4,798,578 | 1/1989 | Ranford | 604/4 |
| 4,822,346 | 4/1989 | Elliott | 604/319 |
| 4,838,872 | 6/1989 | Sherlock | 604/319 |
| 4,857,042 | 8/1989 | Schneider | 604/4 |
| 4,898,593 | 2/1990 | Swisher et al. | 604/319 |
| 4,911,697 | 3/1990 | Kerwin | 604/318 |
| 4,929,244 | 5/1990 | Swisher | 604/319 |
| 4,955,874 | 9/1990 | Farrar et al. | 604/319 |
| 4,979,939 | 12/1990 | Shiber | 606/159 |
| 4,994,050 | 2/1991 | Weilbacher et al. | 604/320 |
| 5,030,201 | 7/1991 | Palestrant | 604/22 |
| 5,041,082 | 8/1991 | Shiber | 604/22 |
| 5,279,601 | 1/1994 | Lichte | 604/319 |
| 5,372,593 | 12/1994 | Boehringer et al. | 609/319 |
| 5,382,244 | 1/1995 | Telang | 604/319 |
| 5,556,380 | 9/1996 | Ridinger et al. | 604/52 |
| 5,688,234 | 11/1997 | Frisbie | 604/22 |

Primary Examiner—Corrine McDermott
Assistant Examiner—Cris L. Rodriguez
Attorney, Agent, or Firm—Sheridan Ross P.C.

[57] ABSTRACT

A medical system for facilitating the removal of body matter including solids, liquids and gases from a body cavity. The system includes mechanical energy applied to the interior surface of a catheter or other type of body drainage conduit to substantially inhibit the adherence of body matter to the catheter, thus minimizing the likelihood of blockage in the catheter. The mechanical energy may be provided by a rotating wire coil, reciprocating wire with collapsible cups or other device to substantially inhibit the adherence of body matter to the catheter and promote flow into a drainage and disposal system

30 Claims, 8 Drawing Sheets

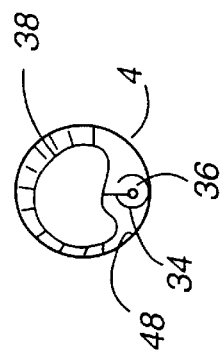
Fig. 6
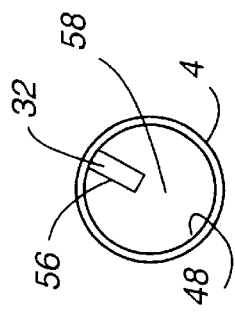
Fig. 5
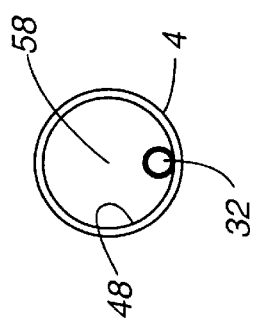
Fig. 4
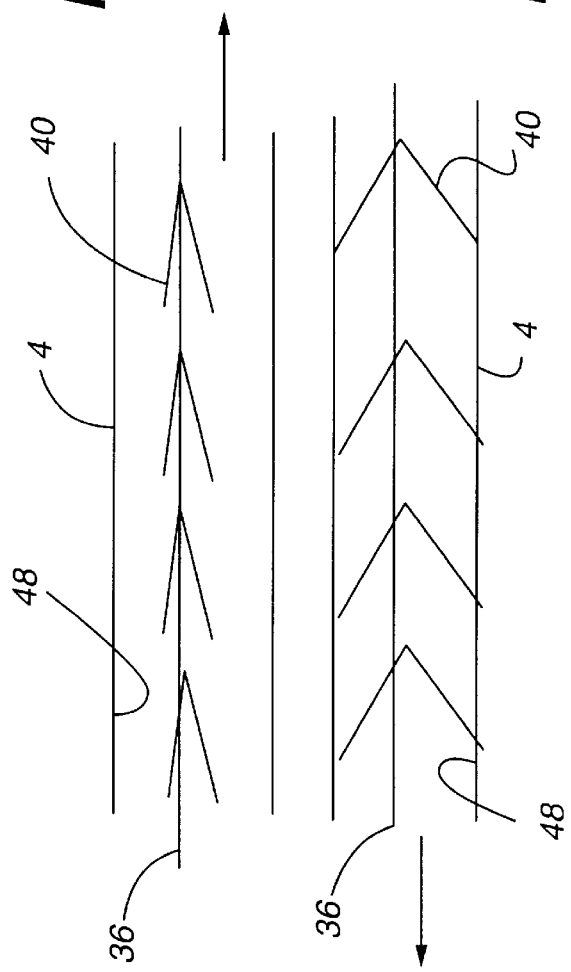
Fig. 7
Fig. 8

BODY FLUIDS AND SOLIDS DRAINAGE SYSTEM

FIELD OF THE SYSTEM

The present invention relates to a system which facilitates the removal of solids, liquids and gases from a body cavity. More particularly, a chest drainage system is described which utilizes mechanical energy to scrape the interior wall surface of a catheter or other drainage conduit to inhibit the attachment of clotted blood or other matter to the interior surface of the catheter, thus substantially reducing the occurrence of blockage.

BACKGROUND OF THE INVENTION

During surgical procedures and post operative recovery periods, it is frequently necessary to drain solids, liquids and gases which may accumulate in a patient's chest cavity. This drainage process substantially reduces the accumulation of liquids and gases in the chest cavities, which can severely impede the medical procedure or prevent the patient from adequately breathing due to the pressure applied to the lungs. This drainage process is most commonly required during recovery from thoracic operations and during surgery as a result of trauma to the chest cavity such as from gun shot wounds or those associated with automobile accidents. The drainage is conducted through one or more catheters and/or a central drainage tube interconnected to the catheters.

During the removal of fluids, solids and other matter from the chest cavity, the catheters commonly become partially or entirely blocked as these materials adhere to the interior wall surface of the catheter and/or central drainage tube. This can create a significant problem during a medical procedure, and is most commonly addressed by the medical staff manually "stripping" or "milking" the catheter to promote the flow of the gas, liquids and solids. This cumbersome procedure is disruptive during a medical procedure (often 1–2 times per hour), takes significant time and may cause extreme discomfort to the patient since the catheter is generally sutured to the patient's surrounding tissue near the catheter access wound. Thus, when the stripping operation is performed, the catheter is often manipulated in a back and forth motion, thus putting tension on the sutures and the patient's interconnected tissue. Finally, the stripping operations may not be entirely effective depending on the nature of the injury or training of the medical staff, thus jeopardizing the patient's well-being and potentially requiring the replacement of the catheter or drainage tube during a medical procedure or during recovery.

SUMMARY OF THE INVENTION

Accordingly, the primary objective of the present invention is to provide a system for facilitating the movement of body matter including solids, semi-solids, liquids and gas from a body cavity without impeded flow or blockage as a result of adherence of this body matter to the interior wall surface of the catheter.

This and other objects of the invention are accomplished by providing a mechanical energy source within the interior of one or more body drainage tubes such as a catheter. The drainage tubes are used in conjunction with suction means for encouraging the movement of body matter from the inlet end of the drainage tube to an outlet end, which is interconnected to a collection chamber for collecting body matter removed from the patient. The mechanical energy may be provided in numerous forms including, but not limited to, a rotating wire coil, reciprocating collapsible cup(s) or vanes, or a magnetic shuttle-cock which moves as a result of alternating electrical current in the wall of the catheter.

In another aspect of the invention the mechanical energy may be provided to a plurality of catheters inserted in a patient's body while commingling the body solids, liquids and gas into a central drainage/gathering tube. This is accomplished by providing mechanical energy within the central drainage/gathering tube and transferring that energy with one or more gears or other energy transferring devices to the plurality of catheters. The bodily fluids, solids and gases are subsequently drained into a fluid collection chamber for safe disposal.

It is another object of the present invention to remove the aforementioned body matter from a body cavity in a manner which reduces vibration and any unnecessary movement of the catheter to increase patient comfort and reduce the likelihood of the catheter becoming detached from the patient's adjoining tissue. In one aspect of the invention, this may be accomplished by providing mechanical energy to the interior wall surface with a rotating wire or wire coil that is driven either manually with a hand operated type of cranking mechanism or more preferably with a motor driven by electricity, air or other means known in the art.

The aforementioned mechanical energy means may be provided in a manner which not only prevents body matter from adhering to the internal walls of the catheter, but which also promotes the movement of fluid from the inlet end to the exit end. Thus, by rotating a plastic coated wire coil or other device at a certain speed and frequency, it is possible to reduce the total suction pressure required to transfer equivalent volumes of body matter at the same rate. This may be accomplished while simultaneously maintaining an open central passageway throughout the interior of the catheter, thus allowing substantially non-obstructive flow of the body matter. Further, based on the effectiveness of the present invention it may not be necessary to provide mechanical energy within the catheter(s) on a continuous basis. Thus, a timer or other type of signalling device may be used to impart mechanical energy at predetermined time intervals In another aspect of the present invention the mechanical energy device such as a wire coil or reciprocating cup has exposed surfaces comprised of one or more materials which will generally not adhere to body matter such as blood, gas or solids such as blood clots or tissue fragments. This material is generally a plastic or organic based polymer such as a fluorinated polymer, including polytetrafluoroethylene (PTFE), or a polyolefin such as polypropylene. Furthermore, the catheter and central gathering/drainage tubes may be comprised of a transparent material which allows the attending medical personnel to monitor the mechanical energy means and movement of body matter through the catheter.

BRIEF DESCRIPTION OF THE DRAWINGS

FIG. 4 is a cross-sectional view of FIG. 3 taken at line 4—4 showing a concentric coil positioned inside the catheter.

FIG. 5 is a cross-sectional view of a rectangular shaped coil inside a catheter.

FIG. 6 is a cross-sectional view of a catheter with an inclosed lumen tube, push-pull support wire and collapsing vanes.

FIG. 7 is a side view of a catheter drainage tube with an internal push-pull wire and interconnected collapsible cups in a collapsed position.

FIG. 8 is a side view of the catheter drainage tube of FIG. 7 with internal push-pull wire and interconnected collapsible cups in an expanded position.

DETAILED DESCRIPTION OF THE PREFERRED EMBODIMENT

Figure 1:
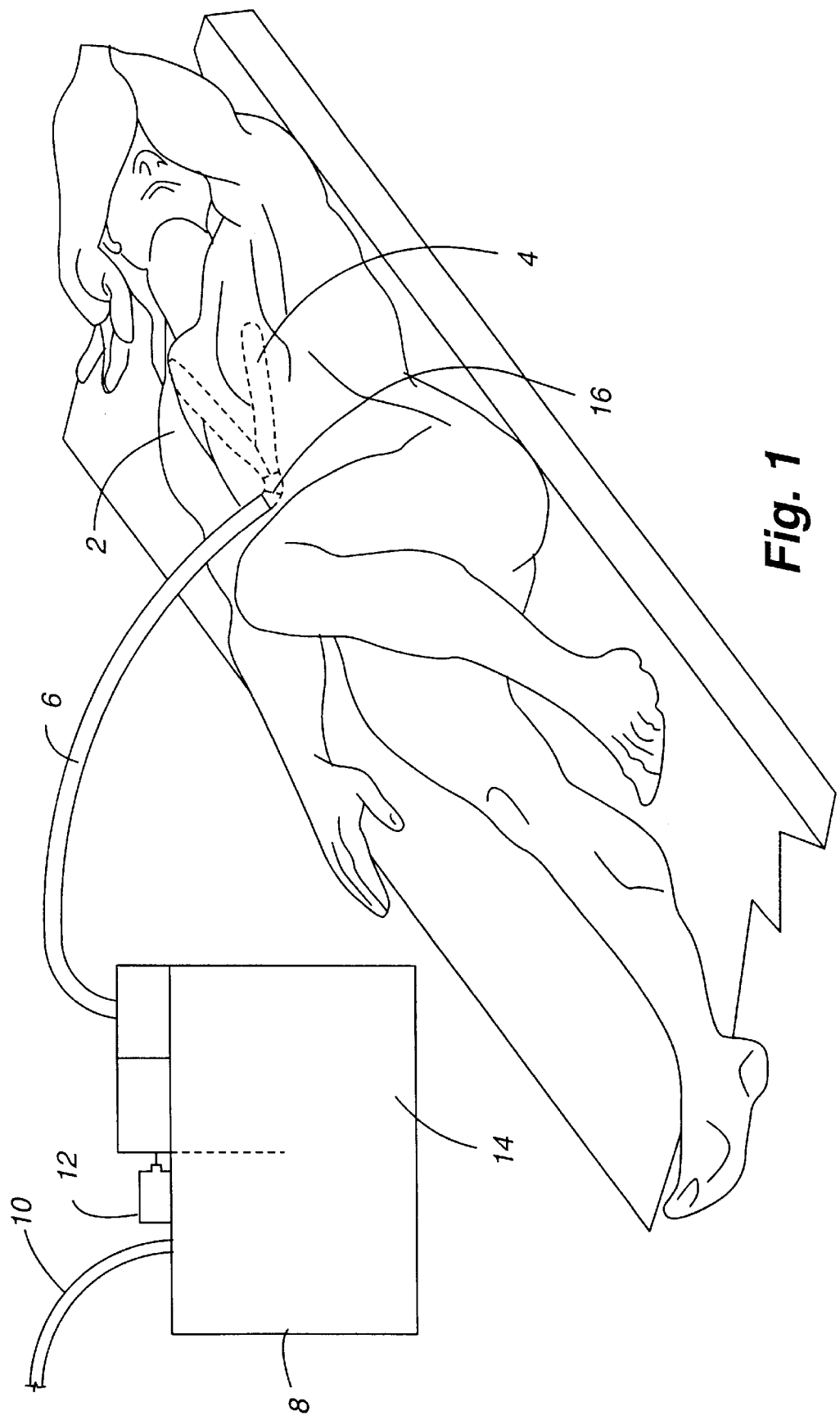
FIG. 1 is a perspective view of the present invention being used on a patient during or after a medical procedure.

Referring now to the drawings, one embodiment of the present invention can be seen in FIG. 1, which generally shows a pair of catheters 4 entering a patient's chest cavity and interconnected to a central drainage/gathering tube 6 and central collection station 8. More specifically the catheters 4 are interconnected at a Y-connector 16 or other type of commingling device which is in communication with a central drainage/gathering tube 6. The central drainage/gathering tube 6 is interconnected to a central collection station 8 where body matter is temporarily collected prior to disposal. In the present context, body matter is defined as any solid, semi-solid, liquid or gas which may be removed from a body cavity. This may include, but is not limited to blood, airs tissue, bone fragments or coagulated blood. A suction line 10 may be used to promote the flow of body matter from the patient's body cavity 2 to the central collection station 8.

In operation, mechanical energy is imparted to the interior wall surface 48 of a catheter 4 or other type of conduit used to transport body matter. This mechanical energy may be in the form of a rotating coil 32, reciprocating collapsible cup 40, magnetic shuttle-cock 44 or other type of device which is capable of scraping on a continuous or non-continuous basis the interior wall surface 48 of the catheter. The scraping action inhibits the adherence of body matter to the interior wall surface 40 of the catheter and additionally may promote the removal of body matter from the body cavity 2 at lower suction pressures. For example, in tests conducted utilizing a wire coil having a cross-sectional diameter of about 1.0 mm which is rotated in a catheter of about 9 mm ID at a speed of 60 RPM, with a suction pressure of about −20 cm $H_2O$, liquid was lifted an additional 8 cm or more compared to what was lifted only by the vacuum. Thus, equivalent volumes of body matter can be removed at reduced suction pressures. However, the exact amount of reduced suction pressure is difficult to quantify based on the wide variety of viscosities of liquid matter and the volume and consistency of solid matter removal.

Figure 2:
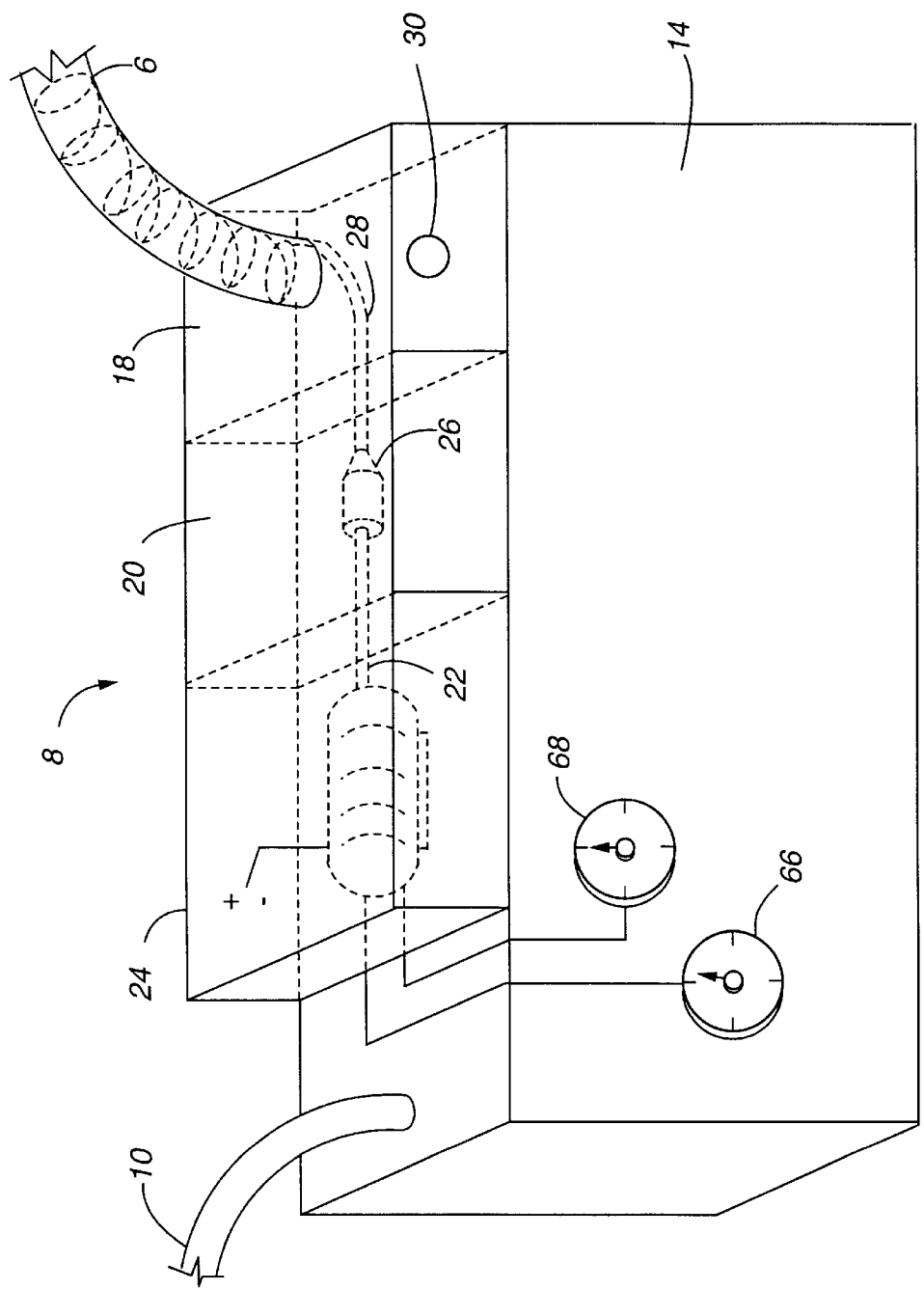
FIG. 2 is a front perspective view of a body matter suction and collection apparatus showing individual components.

The catheter(s) 4 used in the present invention generally have a concentric cross-sectional shape and an internal diameter of between 2 mm and 11 mm although other sizes may be used depending on the application. The central drainage/gathering tube 6 used in the present invention generally has an internal diameter of between about 9.5 mm and 12.7 mm, although other sizes may be used. For removing body matter from the mediastinal or pleural chest cavities, preferably the catheters 4 have an internal diameter of about 6.7 to 8.7 mm while the central drainage/gathering tube 6 has a diameter of about 12.7 mm. To assist the medical staff attending the patient, preferably the catheter(s) 4 and/or central drainage/gathering tube 6 are made of a see-through material such as a flexible plastic or silicone rubber. This allows the medical staff to observe the movement of body matter through the catheter 4 or central drainage/gathering tube 6 to assure there is no blockage or impedance to flow As seen in FIG. 2, the central drainage/gathering tube 6 is interconnected to a central collection station 8 by means of a disengaging chamber 18, which is generally sealed to assure containment of the body matter removed from the body cavity 2. The disengaging chamber 18 receives the body matter which subsequently drains into a fluid collection chamber 14 by means of a fluid collection chamber inlet 30. To promote the flow of body matter into and out of the fluid collection chamber 14, a suction line 10 is generally interconnected to the fluid collection chamber 14. Typically a suction pressure of between about 5 cm $H_2O$ to 25 cm $H_2O$ is applied to the suction line 10.

Figure 12:
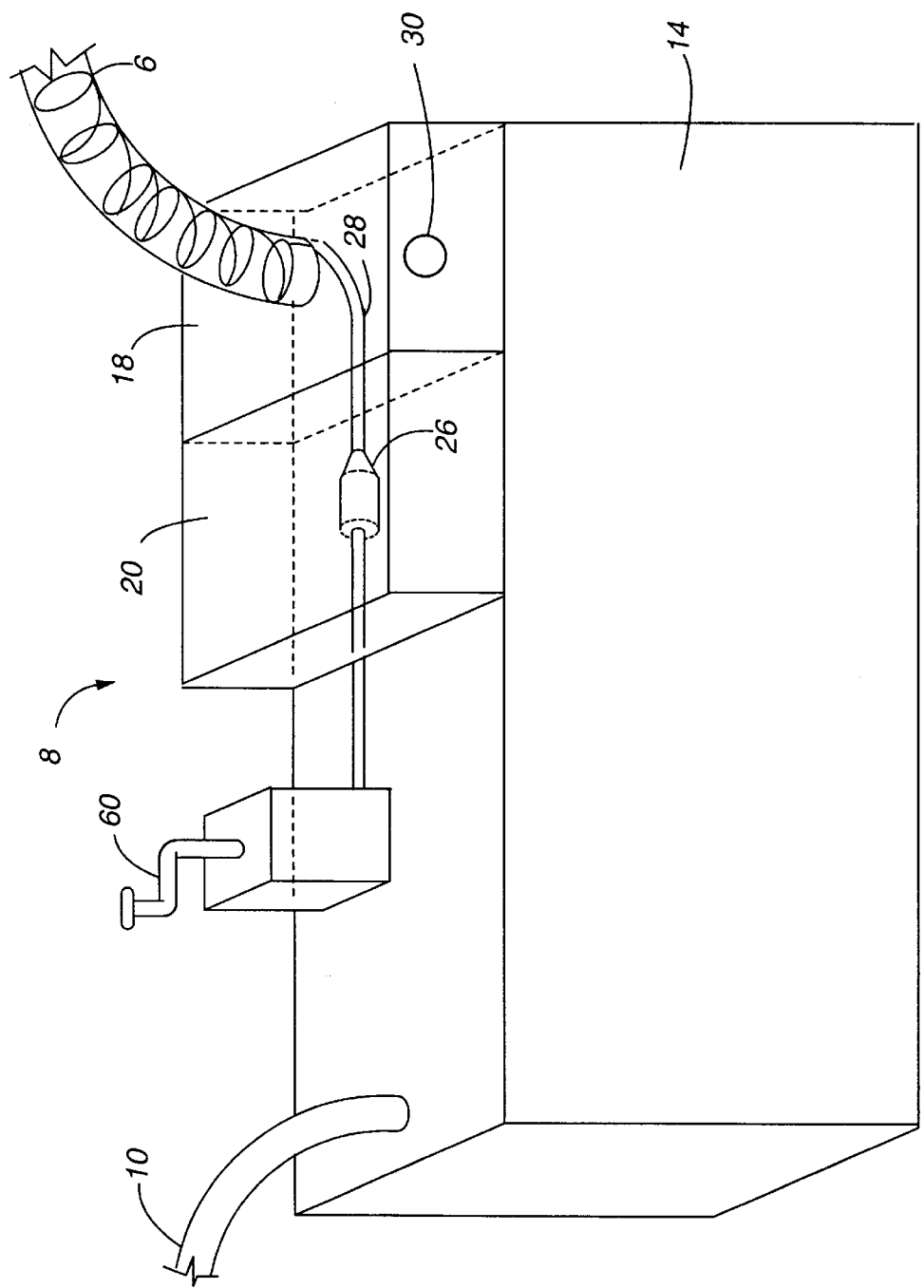
FIG. 12 is a front perspective view of a body matter suction and collection apparatus with manual drive mechanism.

As previously mentioned mechanical energy is provided to the catheter(s) 4 and drainage/gathering tube 6 by means of a rotating coil, reciprocating wire with collapsible cups or with a magnetic shuttle-cock apparatus, although other similar apparatus may be used. The energy is extended to these devices by means of a hand crank 60 or other manual apparatus as seen in FIG. 12 or by means of a motor 12. In one embodiment of the present invention, a motor 12 is provided in a drive chamber 24 located proximate the central collection station 8. The motor may be driven by electricity hydraulic or pneumatic pressure or other means commonly known in the art to turn a drive shaft or provide a reciprocating motion. The motor shaft 22 projects into a seal chamber 20, which is used to assure the containment of any fluid or other body matter which may enter the seal chamber 20 from the disengaging chamber 18. The motor shaft 22 is interconnected to a coil drive end 28 by means of a coupling 26 to allow the transfer of mechanical energy from the motor shaft 22 to the coil 32. The coupling is generally comprised of a direct mechanical connection or a flexible coupling or a keyed coupling, although any similar type of interconnection device may be used.

Figure 3:
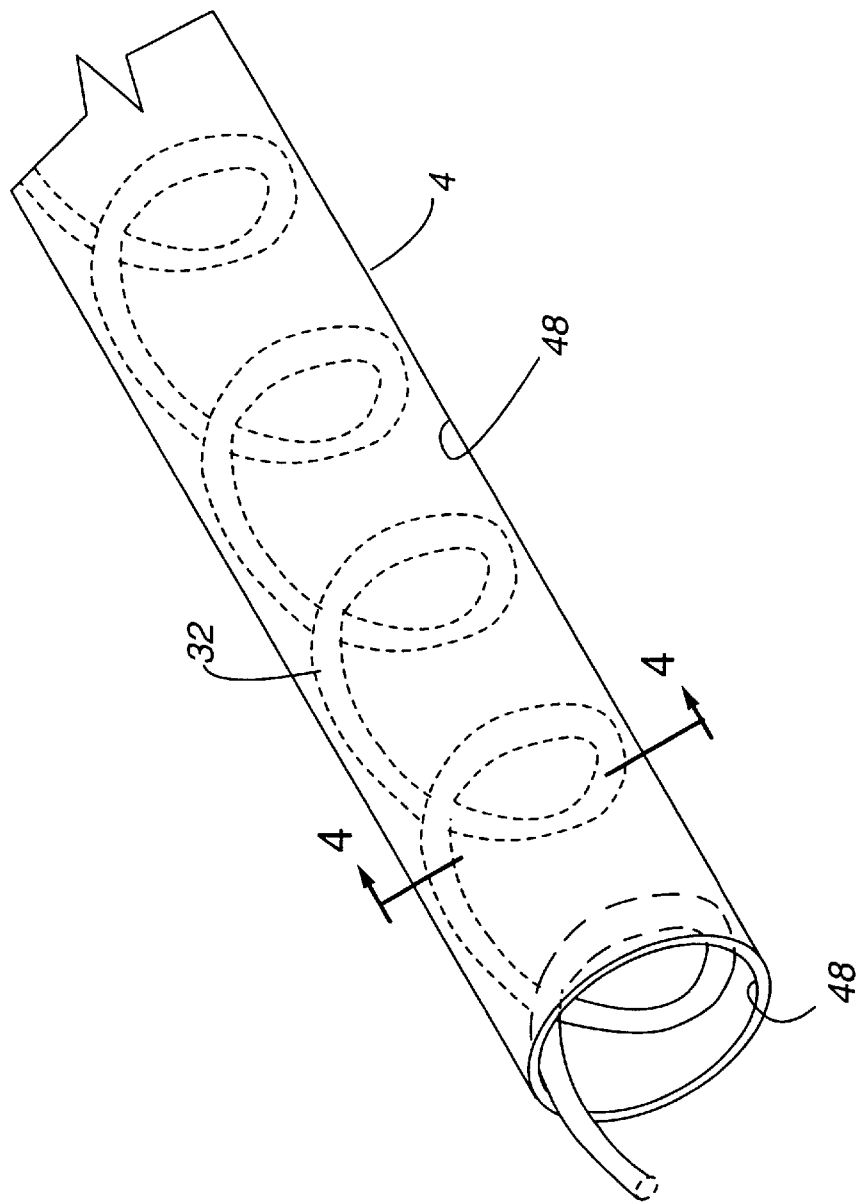
FIG. 3 is a cut-away perspective view of a catheter drainage tube showing a mechanical coil positioned therewithin.

In one embodiment of the present invention, rotational mechanical energy is provided to a wire 32 or other type of semi-rigid, linear material located inside the catheter. As the wire is rotated, a coil 32 begins to naturally form within the confines of the catheter 4 or central drainage/gathering tube 6 as seen in FIG. 3. The rotation and natural coiling effect of the wire allows the coil 32 to scrape the interior wall surface 48 of the catheter 4, this inhibiting any body matter from collecting and impeding flow through the catheter 4. Additionally, a preformed coil 32 may be used in replacement of a linear wire to assure a more consistent scraping action inside the conduit. Preferably, the coil 32 has a rate of twist of between about 0.1 turns per inch and 4 turns per inch. Furthermore, the straight wire or wire coil 32 used in the catheter generally has a cross-sectional diameter of between about 0.25 mm and 2.0 mm and most preferably about 10 mm.

Referring now to FIG. 4, a cross-sectional view of a substantially concentric shaped coil 32 and catheter 4 as seen in FIG. 3 may be viewed. With this embodiment, as the coil 32 is rotated, a central passageway 58 remains open to allow the unobstructed passage of body matter through the catheter 4. In an alternative embodiment, the coil 32 inside the catheter 4 may have a rectangular cross-section as seen in FIG. 5. Any number of geometric configurations may be used for the coil 32, including the attachment of bristles or other devices which serve to scrape the internal wall surface 48 of the catheter 4. For improved efficiency, however, the coil 32 has an exterior surface 56 comprised of a material which will not adhere to the body matter passing through the catheter 4. For example, the coil 32 may be coated with fluoropolymers such as polytetrafluoroethylene, including Teflon®, or other materials with similar properties such as a polyolefin, including polypropylene, polyethylene, or combinations thereof.

In another embodiment of the present invention a push/pull support wire 36 is used in combination with one or more collapsible cups 40 or vanes 38 to provide mechanical energy in the form of a scraping action to the internal wall surface 48 of the catheter 4. This embodiment may be seen in FIGS. 6–8. In operation, as the push/pull support wire 36 is pushed in a forward direction with a lumen support tube 34 (FIGS. 6–7) towards the body cavity 2, the collapsible cups 40 are pivoted to a collapsed position. As the push/pull wire 36 is pulled away from the body cavity 2 (FIG. 8), the vanes 38 or collapsible cups 40 expand and pivot open to a position which pulls or draws the body matter towards the central collection vessel 8, while simultaneously scraping the internal wall surface 48 of the catheter 4.

Figure 9:
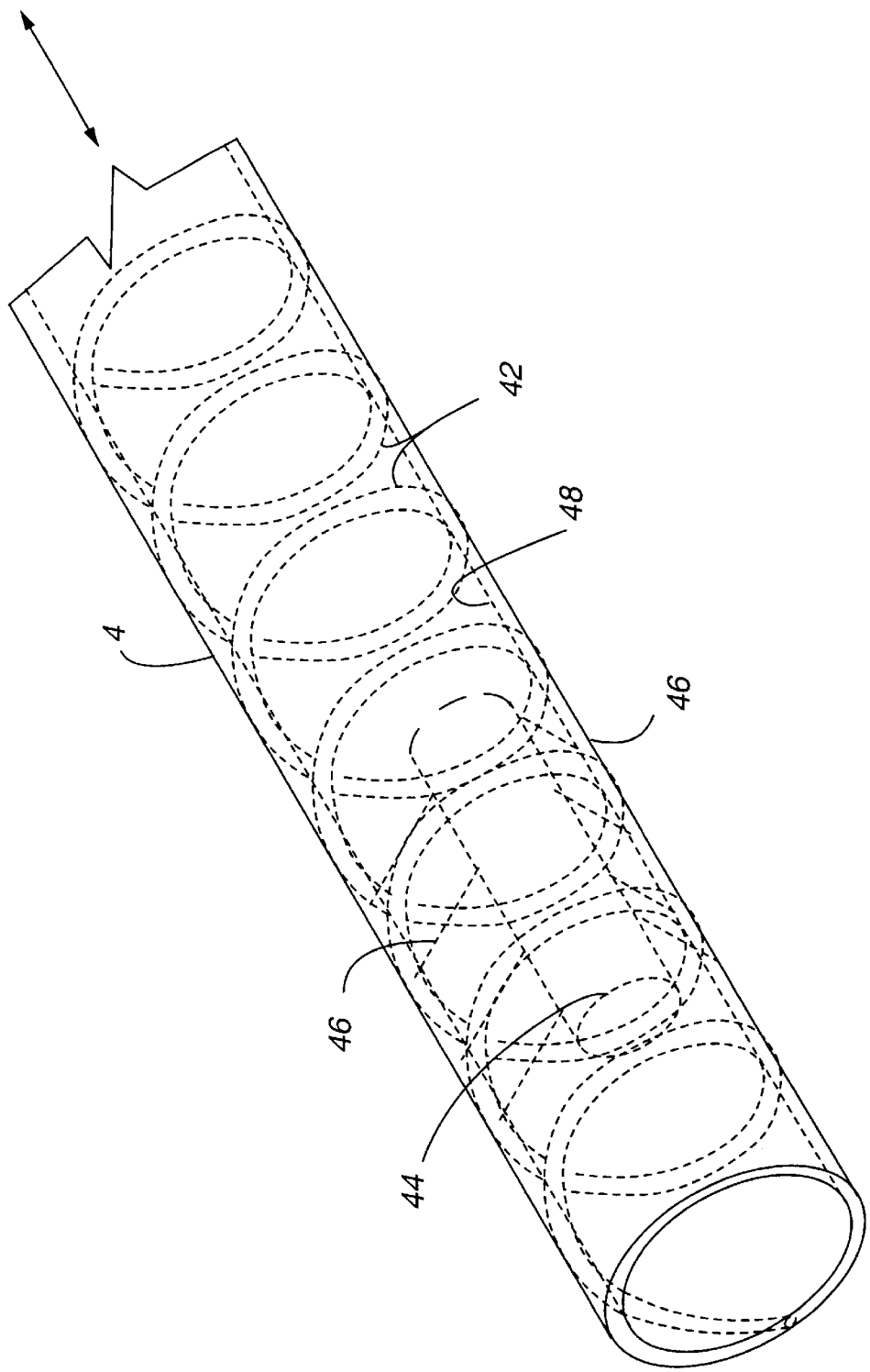
FIG. 9 is a perspective view of a catheter drainage tube with interconnected electrical conduit and internal magnetic shuttle-cock with external vanes

Referring now to FIG. 9, an alternative type of mechanical energy source may be seen in the form of a magnetic shuttle-cock 44 with interconnecting collapsible vanes 46. In operation, the magnetic shuttle-cock 44 is propelled in a reciprocating motion through the catheter 4 by a magnetic field generated by an alternating electrical current flowing through conductive wire 42. The conductive wire 42 is positioned in a generally concentric manner throughout the catheter 4 from the inlet end to the outlet end, where the wire is interconnected to an electrical power source. As electrical current is provided to the conductive wire 42, a magnetic field is generated within the catheter 4 which propels the magnetic shuttle-cock 44 towards the inlet end of the catheter 4. The magnetic shuttle-cock collapsible vanes 46 are oriented to close when traveling in this direction. However, as the direction of current is changed in the conductive wire 42, the magnetic field is reversed and the magnetic shuttle-cock 44 travels towards the outlet end of the catheter 4. In this direction of movement, the magnetic shuttle-cock collapsible vanes 46 pivot open and mechanically scrape the interior wall surface 48 of the catheter 4, thus inhibiting the attachment of any body matter and reducing the probability of blockage in the catheter 4.

The mechanical energy which is used to scrape the interior wall surface 48 of the catheter 4 may be provided either continuously or intermittently depending on the required application. Thus, a timer or other form of signalling or timing device 66 may be used for controlling the frequency upon which mechanical energy is used. Additionally, the speed of rotation or reciprocation or other means employed for mechanical energy may be monitored and controlled with a variable speed control 68 to provide minimum discomfort to the patient as a result of vibration, etc. while providing optimum conditions to promote flow.

Figure 10:
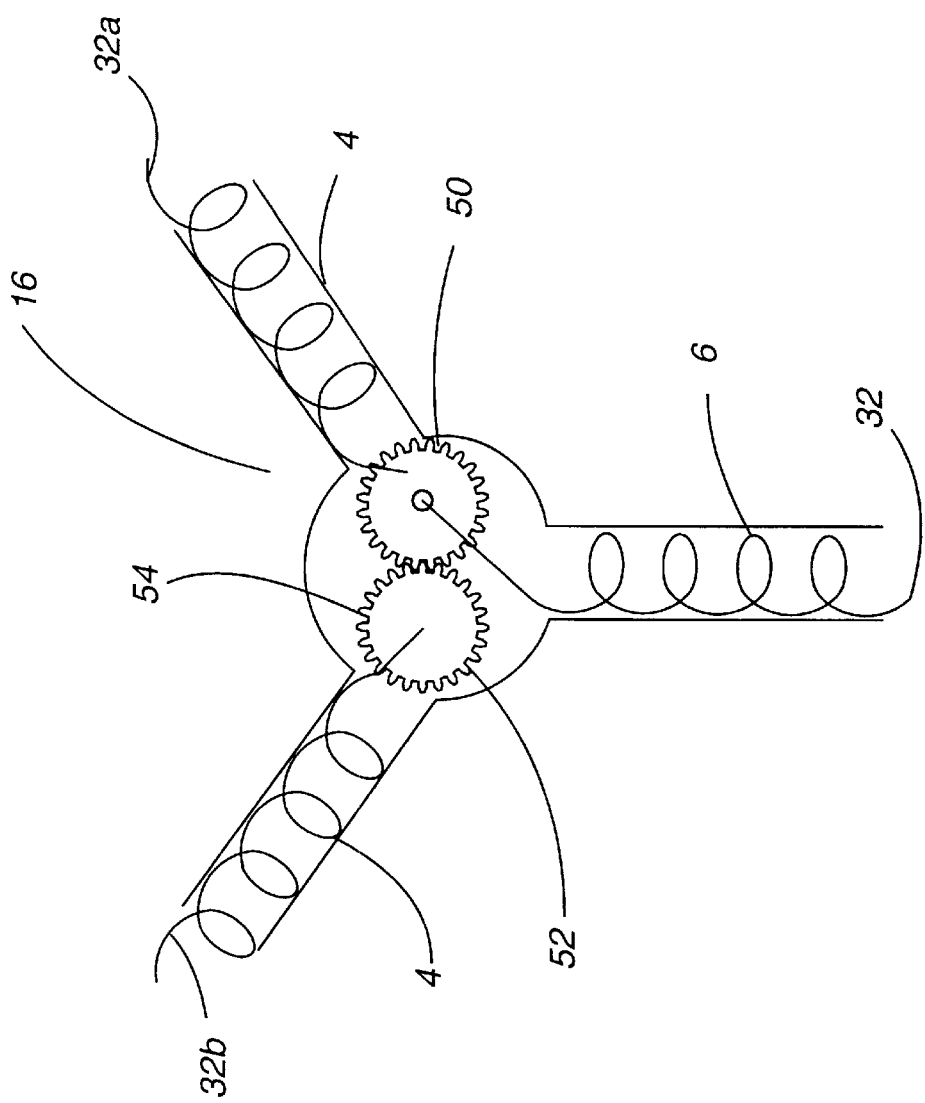
FIG. 10 is a front cutaway view of a y-connector interconnected to a central drainage/gathering tube and two catheters, including drive and transfer gears

Referring now to FIG. 10, a Y-connector 16 is shown which facilitates the commingling of body matter from individual catheters 4 into a central drainage/gathering tube 6. Additionally, the Y-connector 16 is designed to impart mechanical energy from a coil 32 or other mechanical energy device positioned within the central drainage/gathering tube 6 to the coils 32a and 32b positioned within the individual catheters 4.

The transfer of mechanical energy is achieved by the use of a gear assembly which includes a drive gear 50 operably interconnected to a transfer gear 52 by means of gear teeth 54. However, other forms of energy transfer mechanisms may be used, such as a belt or chain. In operation, the coil 32 or other form of mechanical energy in the central drainage/gathering tube 6 is interconnected to the drive gear 50. The coil 32 is interconnected to the drive gear by means of a hook eye (not shown) or other attachment device which permits the rotation energy in the coil to be transferred to the drive gear 50. Depending on the size and type of wire coil used, the coil 32 may be interconnected to middle of the drive gear 50, or offset towards the gear teeth 54. As coil 32 is rotated in the central drainage/gathering tube 6, the drive gear 50 imports energy to and rotates the transfer gear 52. Both the drive gear 50 and transfer gear 52 are interconnected to coil 32a and 32b, respectively or other mechanical energy means located in individual catheters 4. Thus, as the coil 32 rotates in the central drainage/gathering tube 6, energy is imported to coils 32a and 32b positioned within the individual catheters 4 through the drive gear 50 and transfer gear 52. As will be appreciated by one skilled in the art, this type of commingling device and gear assembly may be used for two or more catheters 4, depending on the required application.

Figure 11:
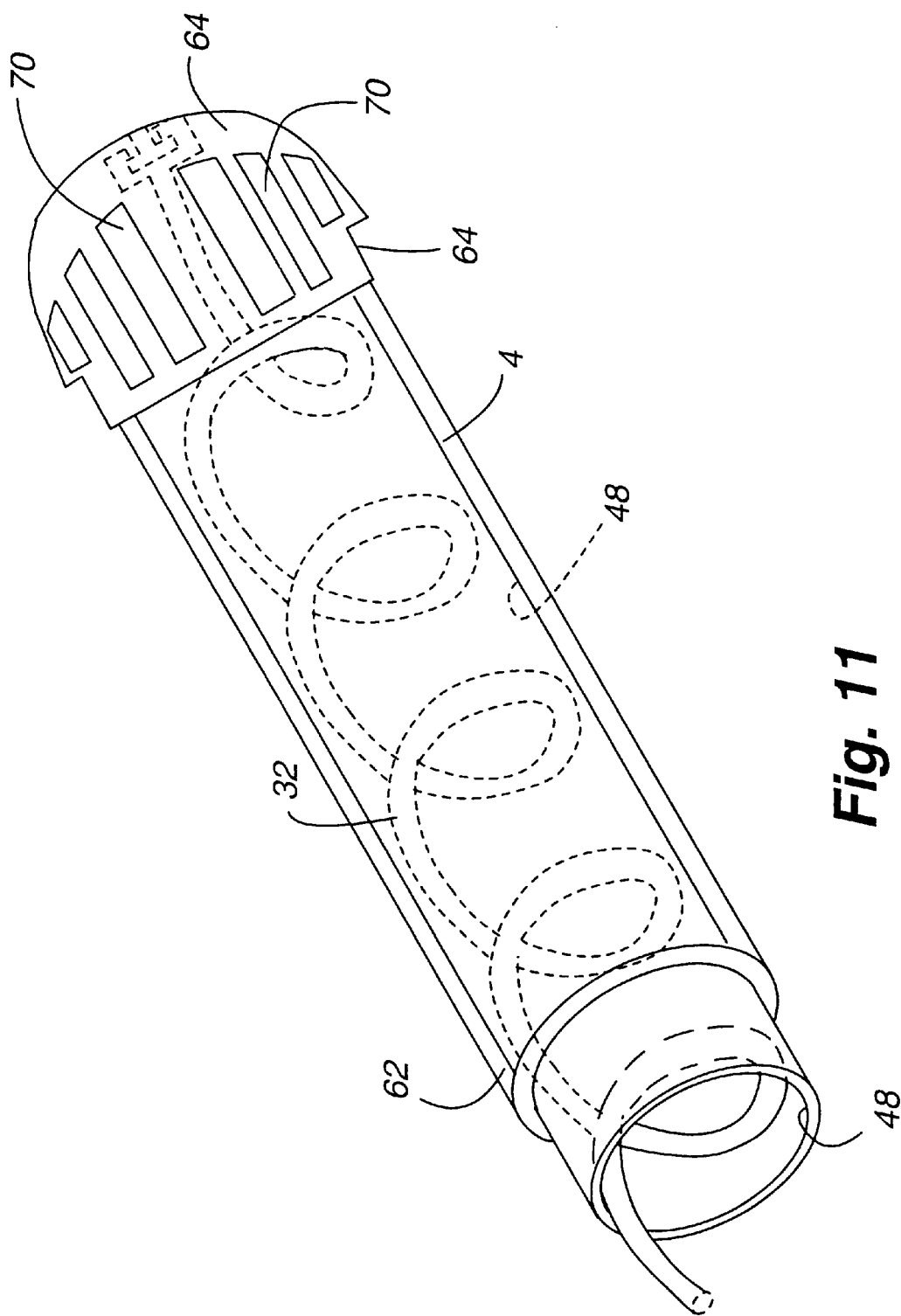
FIG. 11 is a cut-away perspective view of a catheter drainage tube with an end cap and a sheath enclosing the catheter.

Referring now to FIG. 11, in one embodiment of the present invention an end cap 64 is interconnected to an inlet end of the drainage tube 6. The end cap 64 has communication ports 70 to allow the ingress of body matter from said body cavity. In an alternative embodiment the end cap 64 has an engagement means for supporting a second end of the coil 32 disposed within the drainage tube 6.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

For clarity, the numbering of various components as identified in the drawings are included herein:

| | | | |
|---|---|---|---|
| 2 | Patient Chest Cavity | 40 | Collapsible Cup |
| 4 | Catheters | 42 | Conductive Wire |
| 6 | Drainage/Gathering Tube | 44 | Magnetic Shuttle- |
| 8 | Central Collection Vessel | | cock |
| 10 | Suction Line | 46 | Shuttle-cock |
| 12 | Motor | | Collapsible Vanes |
| 14 | Fluid Collection Chamber | 48 | Catheter Interior |
| 16 | Y-Connector | | Wall Surface |
| 18 | Disengaging Chamber | 50 | Drive Gear |
| 20 | Seal Chamber | 52 | Transfer Gear |
| 22 | Motor Shaft | 54 | Gear Teeth |

-continued

| 24 | Drive Chamber | 56 | Coil Exterior |
| --- | --- | --- | --- |
| 26 | Coupling | | Surface |
| 28 | Coil Drive End | 58 | Central Passageway |
| 30 | Fluid Collection Chamber Inlet | 60 | hand crank |
| 32 | Coil in Central Drainage Tube | 62 | exterior sheath |
| 32a | Catheter Coil | 64 | end cap |
| 32b | Catheter Coil | 66 | timing device |
| 34 | Lumen Support Tube | 68 | variable speed control |
| 36 | Push/Pull Support wire | 70 | end cap communication |
| 38 | Vane | | ports |

What is claimed is:

1. A medical drainage system for removing body matter from a body cavity, consisting essentially of:

at least one drainage tube for insertion into said body cavity, said drainage tube having an interior surface, an exterior surface, a substantially open inlet end for receiving said body matter, and an outlet end for discharging said body matter;

collection means positioned proximate to said outlet end of said drainage tube to collect said body matter;

suction means in operative communication with said collection means for creating a lower pressure at said outlet end of said drainage tube than at said inlet end; and mechanical energy means comprising at least one selectively rotatable wire coil acting independently and without interconnection to any invasive apparatus, said rotatable wire coil operatively disposed within said drainage tube for scraping said interior surface of said drainage tube, said wire coil having a first end operatively positioned proximate said collection means and a second end positioned proximate said inlet end, wherein said body matter is inhibited from collecting on said interior surface of said drainage tube and is transported from said inlet end of said drainage tube to said collection means, said drainage tube having an unobstructed central passageway extending substantially from said inlet end to said outlet end to facilitate the unimpeded flow of said body matter through said drainage tube.

2. The medical drainage system of claim 1, wherein said body matter comprises solids, semi-solids, liquids and gas.

3. The drainage system of claim 1, further comprising drive means interconnected to a first end of said mechanical energy means to provide mechanical energy to said mechanical energy means.

4. The medical drainage system of claim 3, wherein said drive means is motorized.

5. The medical drainage system of claim 3, further comprising variable speed means interconnected to said drive means, wherein the amount of energy provided to said mechanical energy means can be adjusted.

6. The medical drainage system of claim 3, wherein said drive means is manually operated.

7. The drainage system of claim 1, wherein said drainage tube is flexible to permit bending.

8. The drainage system of claim 1, wherein said drainage tube is comprised of a see-through material.

9. The drainage system of claim 1, wherein said suction means comprises a suction tube interconnected to said collection means.

10. The medical drainage system of claim 1, herein said rotatable wire has a substantially rectangular cross-section.

11. The medical drainage system of claim 1, wherein said selectively rotatable wire has an exterior surface which resists the adherence of said body matter, said exterior surface comprising at least polyolefin or fluoropolymer materials.

12. On line 2, please delete the word "cup" and replace with the word "cap".

13. The medical drainage system of claim 1, wherein said mechanical energy means scrapes said interior surface of said drainage tube in a substantially continuous manner.

14. The medical drainage system of claim 1, further comprising timing means in operative communication with said drive means, wherein said mechanical energy means scrapes said interior surface of said drainage tube in a non-continuous manner at selected time intervals.

15. The medical drainage device of claim 1, further comprising an exterior sheath substantially enclosing said drainage tube, wherein the amount of vibration felt by a patient utilizing said medical drainage device is minimized.

16. A medical drainage apparatus for removing body matter from a body cavity, comprising:

a plurality of body drainage tubes, each of said drainage tubes having an inlet end, an outlet end, an interior surface and an exterior surface;

a central gathering tube having a first end, a second end, an interior surface and an exterior surface;

merging means for sealingly interconnecting each of said outlet ends of said plurality of drainage tubes to said first end of said central gathering tube;

collection means positioned proximate said second end of said central gathering tube to collect said body matter;

suction means in operative communication with said collection means for creating a lower pressure at said second end of said central gathering tube than at said inlet ends of said plurality of drainage tubes;

mechanical energy means operatively positioned within each of said plurality of drainage tubes and said central gathering tube for scraping said interior surfaces of said drainage tubes and said central gathering tube to prevent said body matter from impeding flow of said body matter from said inlet ends of said drainage tubes to said second end of said central gathering tube; and coordinating means located within said merging means for operatively interconnecting said mechanical energy means in said central gathering tube to said mechanical energy means in each of said drainage tubes.

17. The medical apparatus of claim 16, further comprising drive means interconnected to said mechanical energy means for providing mechanical energy to said mechanical energy means within said central gathering tube and said plurality of drainage tubes.

18. The medical apparatus of claim 17, further comprising variable speed means, interconnected to said drive means whereby the amount of energy provided to said mechanical energy means can be adjusted.

19. The medical apparatus of claim 17, wherein said drive means is manually driven.

20. The medical apparatus of claim 17, wherein said drive means is motorized.

21. The medical apparatus of claim 16, wherein said mechanical energy means comprises at least one selectively rotatable wire with a substantially circular cross-section, said wire having a first end operatively positioned proximate said collection means and a second end positioned proximate said inlet end of said drainage tube.

22. The medical apparatus of claim 16, wherein said mechanical energy means comprises at least one selectively rotatable wire with a substantially rectangular cross-section, said wire having a first end operatively positioned proximate said collection means and a second end positioned proximate said inlet end of said drainage tube.

23. The medical apparatus of claim 16, wherein said mechanical energy means comprises at least one selectively rotatable wire coil, said wire coil having a first end operatively positioned proximate said collection means and a second end positioned proximate said inlet ends.

24. The medical apparatus of claim 16, further comprising timing means to provide mechanical energy to said mechanical energy means on a predetermined time interval.

25. The medical drainage apparatus of claim 16, wherein said coordinating means comprises:

(a) a drive gear having a first end, a second end, and a plurality of teeth interposed therebetween, said first end interconnected to said mechanical energy means in said central gathering tube and said second end interconnected to said mechanical energy means in a first body drainage tubes (b) a transfer gear having a first end, a second end and a plurality of teeth interposed therebetween, said second end interconnected to said mechanical energy means in a second body drainage tube and said teeth operatively engaged with said teeth of said drive gears wherein when said mechanical energy means in said central gathering tube is rotated, said drive gear rotates said transfer gear providing mechanical energy to said mechanical energy means in said first body drainage tube, said second body drainage tube and said central gathering tubes.

26. The medical drainage device of claim 16, wherein said body matter comprises liquid, solids, semi-solids and gas.

27. The medical apparatus of claim 16, wherein said central gathering tube and said body drainage tubes are comprised of a flexible, substantially transparent material.

28. The medical apparatus of claim 16, wherein said mechanical energy means has an outer surface comprised of a material which resists the adherence of said body matter.

29. A medical drainage system for removing body matter from a body cavity consisting essentially of:

at least one drainage tube for insertion into said body cavity, said drainage tube having an interior surface, an exterior surface, a substantially open inlet end for receiving said body matter, and an outlet end for discharging said body matter;

collection means positioned proximate to said outlet end of said drainage tube to collect said body matter;

suction means in operative communication with said collection means for creating a lower pressure at said outlet end of said drainage tube than at said inlet end;

mechanical energy means operatively disposed within said drainage tube for scraping said interior surface of said drainage tube, said mechanical energy means acting independently and without interconnection to any invasive apparatus, wherein said body matter is inhibited from collecting on said interior surface of said drainage tube and is transported from said inlet end of said drainage tube to said collection means, said drainage tube having an unobstructed central passageway extending substantially from said inlet end to said outlet end to facilitate the unimpeded flow of said body matter through said drainage tube;

drive means interconnected to a first end of said mechanical energy means to provide mechanical energy to said mechanical energy means; and variable speed means interconnected to said drive means, wherein the amount of energy provided to said mechanical energy means can be adjusted.

30. A medical drainage system for removing body matter from a body cavity, consisting essentially of:

at least one drainage tube for insertion into said body cavity, said drainage tube having an interior surface, an exterior surface, a substantially open inlet end for receiving said body matter, and an outlet end for discharging said body matter;

collection means positioned proximate to said outlet end of said drainage tube to collect said body matter;

suction means in operative communication with said collection means for creating a lower pressure at said outlet end of said drainage tube than at said inlet end;

mechanical energy means operatively disposed within said drainage tube for scraping said interior surface of said drainage tube, said mechanical energy means acting independently and without interconnection to any invasive apparatus, wherein said body matter is inhibited from collecting on said interior surface of said drainage tube and is transported from said inlet end of said drainage tube to said collection means; and timing means in operative communication with said drive means, wherein said mechanical energy means scrapes said interior surface of said drainage tube in a non-continuous manner at selected time intervals.

* * * * *